United States Patent
Takizawa et al.

(10) Patent No.: US 8,462,406 B2
(45) Date of Patent: Jun. 11, 2013

(54) SPECTRAL COLORIMETRIC APPARATUS AND IMAGE FORMING APPARATUS USING THE SAME

(75) Inventors: Tokuji Takizawa, Utsunomiya (JP); Kazumi Kimura, Toda (JP); Nobuyuki Tochigi, Kawaguchi (JP); Masayasu Teramura, Utsunomiya (JP)

(73) Assignee: Canon Kabushiki Kaisha (JP)

( * ) Notice: Subject to any disclaimer, the term of this patent is extended or adjusted under 35 U.S.C. 154(b) by 481 days.

(21) Appl. No.: 12/769,247

(22) Filed: Apr. 28, 2010

(65) Prior Publication Data
US 2010/0278543 A1   Nov. 4, 2010

(30) Foreign Application Priority Data

Apr. 30, 2009   (JP) .................................. 2009-110884
Mar. 30, 2010   (JP) .................................. 2010-077821

(51) Int. Cl.
*H04N 1/46* (2006.01)
*G01J 3/28* (2006.01)
*G03G 15/04* (2006.01)
*G03G 15/00* (2006.01)

(52) U.S. Cl.
USPC ........... 358/509; 358/504; 356/326; 356/328; 399/32; 399/72

(58) Field of Classification Search
USPC ... 358/504, 505, 509, 510, 511, 1.9; 356/326, 356/328; 399/9, 32, 72
See application file for complete search history.

(56) References Cited

U.S. PATENT DOCUMENTS

| | | | | |
|---|---|---|---|---|
| 4,540,282 A | * | 9/1985 | Landa et al. | 356/328 |
| 4,707,056 A | * | 11/1987 | Bittner | 385/31 |
| 5,343,289 A | * | 8/1994 | Crawford et al. | 356/328 |
| 5,489,980 A | * | 2/1996 | Anthony | 356/308 |
| 5,798,831 A | * | 8/1998 | Hagiwara | 356/237.2 |

(Continued)

FOREIGN PATENT DOCUMENTS

| EP | 0 440 443 A2 | 8/1991 |
|---|---|---|
| JP | 6-050814 A | 2/1994 |

(Continued)

OTHER PUBLICATIONS

Kimura, Kazumi et al. "Spectral Colorimetric Apparatus and Color Image Forming Apparatus Using the Same", Specification and Drawings of unpublished related co-pending U.S. Appl. No. 12/769,282, filed Apr. 28, 2010. pp. 1-63.

*Primary Examiner* — Madelein A Nguyen
(74) *Attorney, Agent, or Firm* — Rossi, Kimms & McDowell LLP

(57) ABSTRACT

A spectral colorimetric apparatus for detecting a color of an image of a subject, including: an illumination optical system illuminating the subject on a detection surface; a spectral optical system including a spectral element spectrally separating the beam diffused by the subject and a light receiving element array detecting a spectral intensity distribution; and a guiding optical system for guiding a beam diffused by the subject, wherein: the detection surface is parallel to a spectral plane including a principal ray of a beam entering the spectral optical system and a principal ray of a beam spectrally separated; the principal ray of the beam enters the spectral optical system within the spectral plane obliquely to a line joining a center of the light receiving element array with a surface vertex of the spectral element; and a light receiving surface of the light receiving element array is orthogonal to the spectral plane.

8 Claims, 6 Drawing Sheets

U.S. PATENT DOCUMENTS

| | | | |
|---|---|---|---|
| 5,880,834 A * | 3/1999 | Chrisp | 356/328 |
| 6,597,451 B1 * | 7/2003 | Araki | 356/328 |
| 6,606,156 B1 | 8/2003 | Ehbets et al. | |
| 7,173,695 B2 * | 2/2007 | Katsunuma | 356/326 |
| 7,365,850 B2 * | 4/2008 | Imura | 356/419 |
| 8,184,289 B2 * | 5/2012 | Kimura et al. | 356/326 |
| 2002/0176151 A1 * | 11/2002 | Moon et al. | 359/298 |
| 2005/0088705 A1 * | 4/2005 | Okamoto et al. | 358/474 |
| 2006/0114470 A1 * | 6/2006 | Takashima et al. | 356/453 |
| 2008/0225291 A1 * | 9/2008 | Konno et al. | 356/328 |
| 2009/0059226 A1 * | 3/2009 | Kajiki et al. | 356/328 |
| 2009/0059228 A1 * | 3/2009 | Horie et al. | 356/369 |
| 2010/0150610 A1 * | 6/2010 | Maeda et al. | 399/159 |
| 2010/0278543 A1 * | 11/2010 | Takizawa et al. | 399/9 |
| 2010/0284084 A1 * | 11/2010 | Ishibe | 359/571 |
| 2011/0080584 A1 * | 4/2011 | Ko | 356/328 |

FOREIGN PATENT DOCUMENTS

| | | |
|---|---|---|
| JP | 6-058812 A | 3/1994 |
| JP | 6-094528 A | 4/1994 |
| JP | 9-160343 A | 6/1997 |
| JP | 2000-298066 A | 10/2000 |
| JP | 2001-264173 A | 9/2001 |
| JP | 2002-206967 A | 7/2002 |
| JP | 2004-126278 A | 4/2004 |

* cited by examiner

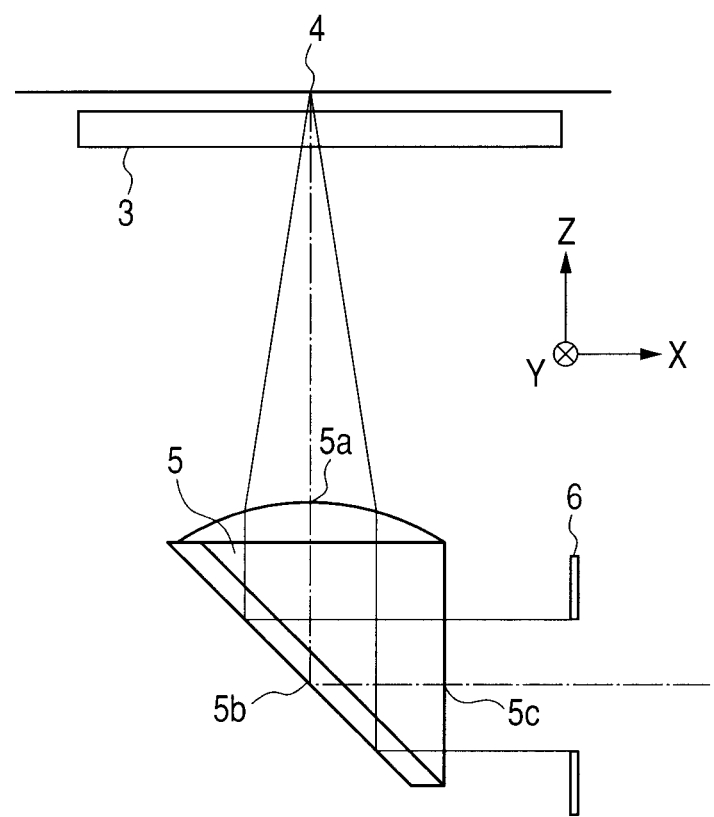

SPECTRAL COLORIMETRIC APPARATUS AND IMAGE FORMING APPARATUS USING THE SAME

BACKGROUND OF THE INVENTION

1. Field of the Invention

The present invention relates to a color sensor using a diffraction grating for color recognition or colorimetry on a subject and, more particularly, is suitable for a color sensor which is incorporated in a color image forming apparatus to perform colorimetry on toner or printing media.

2. Description of the Related Art

In an image forming apparatus for forming a color image through an electrophotographic process, a deviation in color tone may occur because of color mixing of toner. The same problem occurs, not only in the electrophotographic type image forming apparatus but also in general image forming apparatuses for forming a color image such as an ink-jet type image forming apparatus. In the electrophotographic type, particularly, drum sensitivity, the charge capacity of toner, and transfer efficiency to a paper sheet are changed for each color depending on the condition of environment, and hence a color mixing ratio is deviated from a predetermined value and thus it is highly likely to affect a color tone. Further, there is a need for the realization of higher-degree of color tone reproduction in the print industry.

In order to solve the problems described above, Japanese Patent Application Laid-Open No. H09-160343 proposes a method of measuring a spectral reflection light quantity of a toner image using two different spectral filters and correcting an image signal based on the result of the measurement. Similarly, Japanese Patent Application Laid-Open No. 2004-126278 proposes an image forming apparatus for performing color tint correction on a color image. In the electrophotographic type image forming apparatus, according to Japanese Patent Application Laid-Open No. 2004-126278, a color tint detection sensor is provided in the downstream of a fixing device located on a fixing and conveying path to detect RGB output values of colors of a mixed color patch image formed on a transferring material (printed image) moving along a conveying path.

In order to determine the color tone at higher precision, it is necessary to increase the number of spectral wavelength bands to at least three, which corresponds to the number of primary colors. When the number of wavelength bands may be further increased, the color tone may be determined at higher precision. In order to increase the number of wavelength bands, there have been proposed a large number of diffraction spectral devices for performing spectral measurement based on a diffraction phenomenon, for example, in Japanese Patent Application Laid-Open No. H06-058812, Japanese Patent Application Laid-Open No. H06-050814 and Japanese Patent Application Laid-Open No. 2001-264173.

An example of a colorimetric device capable of measuring absolute chromaticity at high wavelength resolution is a spectral colorimetric apparatus for obtaining chromaticity from a spectral intensity distribution using a diffraction spectroscope.

FIG. 9 illustrates a Rowland type diffraction spectral colorimetric apparatus generally used as a conventional diffraction spectral device.

A light beam to be detected is entered into a detection optical apparatus from an incident window 108. Specifically, scattering light from a subject illuminated by an illumination optical system (not shown) is entered into the detection optical apparatus from a stop. The light is spectrally separated by a concave reflective diffraction element 104 and then obtained as a spectral intensity distribution by a one-dimensional array detector 103.

In a color image forming apparatus for forming a color image as illustrated in FIG. 8, the spectral colorimetric apparatus is required to be incorporated for use into the main body of the color image forming apparatus. In practice, a reduction in size of the spectral colorimetric apparatus in a conveying direction of a printed paper sheet, that is, in a direction perpendicular to a detection surface is strongly demanded so as not to hinder the conveying of the printed paper sheet in the color image forming apparatus.

The image forming apparatuses disclosed in Japanese Patent Application Laid-Open No. H09-160343 and Japanese Patent Application Laid-Open No. 2004-126278 employ a colorimetric device using an RGB filter. The colorimetric device is small in size but the number of wavelength bands is small, and thus is not suitable to measure accurate absolute chromaticity. Further, when the number of filters is to be increased, there is a problem that a significant increase in cost occurs.

In the case of a Rowland type spectral device, which is generally used as the diffraction spectral device, imaging magnification effected by the diffraction grating shows substantially qui-magnification, that is, the ratio of the size of the stop and the image thereof on the array detector are substantially 1. When a Rowland circle is made smaller, the spectral unit may be relatively easily reduced in size. However, when the entire structure including the illumination system is taken into account, there is still room for improvement. In the device disclosed in Japanese Patent Application Laid-Open No. H06-058812, the detection surface and the spectral plane are perpendicular to each other, and hence the device is increased in size in a direction perpendicular to the detection surface. In the device disclosed in Japanese Patent Application Laid-Open No. H06-050814, a test subject and a stop are made conjugate with each other so that a light beam to be detected which is emitted from the test subject forms an image on a stop through a mirror and an imaging lens. The optical path of the light beam to be tested is folded by the mirror to reduce the device in size. However, the detection surface and the spectral plane are made perpendicular to each other, and hence the device is increased in size in the direction perpendicular to the detection surface.

There is another problem that, when the entire apparatus including the illumination system is reduced in size, it is difficult to remove flare light from the illumination system. When the flare light reaches a sensor, a noise is superimposed on an output of the sensor, making it difficult to perform accurate chromaticity measurement.

SUMMARY OF THE INVENTION

The present invention has been bade in view of the problems describe above, and therefore, it is an object of the present invention to provide a spectral colorimetric apparatus which may be significantly reduced in size in a direction perpendicular to a detection surface while effectively reducing a noise caused by flare light due to the reduction in size and is suitable for an image forming apparatus.

In order to attain the above-mentioned object, the present invention provides a spectral colorimetric apparatus for detecting a color of an image of a test subject illuminated, including; an illumination optical system for illuminating the test subject located on a detection surface, a spectral optical system including a spectral element which spectrally separates the light beam diffused by the test subject and a light receiving element array which detects a spectral intensity distribution, and a guiding optical system for guiding a light beam diffused in the test subject, in which; when a plane including a principal ray of a light beam incident on the spectral optical system and a principal ray of a light beam having been subjected to the spectral separation by the spectral element is defined as a spectral plane, the detection surface and the spectral plane are parallel to each other, the principal ray of the light beam enters the spectral optical system within the spectral plane enters obliquely with respect to a straight line joining a center of the light receiving element array with a surface vertex of the spectral element, and the light receiving surface of the light receiving element array and the spectral plane are orthogonal to each other.

According to the present invention, the thickness of the spectral colorimetric apparatus in the direction perpendicular to the detection surface may be reduced to a value significantly smaller than that of a conventional spectral apparatus. Further, when the spectral colorimetric apparatus is combined with a Rowland type spectral system, a maximum reduction in size may be achieved by a minimum structure. Therefore, the spectral colorimetric apparatus is easily incorporated in an image forming apparatus or the like, and hence a paper sheet conveying unit which is usually located after a fixing device may be made more compact. In this manner, the spectral colorimetric apparatus also contributes to reduce the size of the image forming apparatus. Still further, the spectral colorimetric apparatus is reduced in thickness, and hence the conveyance of the paper sheet is not hindered. Thus, high-precision chromaticity measurement may be performed without changing a process speed.

Further, the illumination light source and the light receiving element array are disposed with a reference axis of the spectral unit sandwiched therebetween, and hence a noise caused by direct flare light from the illumination optical source may be significantly reduced, which allows stable and high-precision chromaticity measurement to be performed. Therefore, more stable and high-precision color reproduction may be achieved by the image forming apparatus.

Further features of the present invention become apparent from the following description of exemplary embodiments with reference to the attached drawings.

BRIEF DESCRIPTION OF THE DRAWINGS

FIG. 5 is a principal cross sectional view (taken along the line 5-5 of FIG. 2) illustrating a guiding optical system of the spectral colorimetric apparatus according to Embodiment 1 of the present invention.

DESCRIPTION OF THE EMBODIMENTS

Hereinafter, exemplary embodiments of the present invention are described in detail with reference to the attached drawings.

Embodiment 1

A spectral colorimetric apparatus according to Embodiment 1 of the present invention is described.

Figure 1:
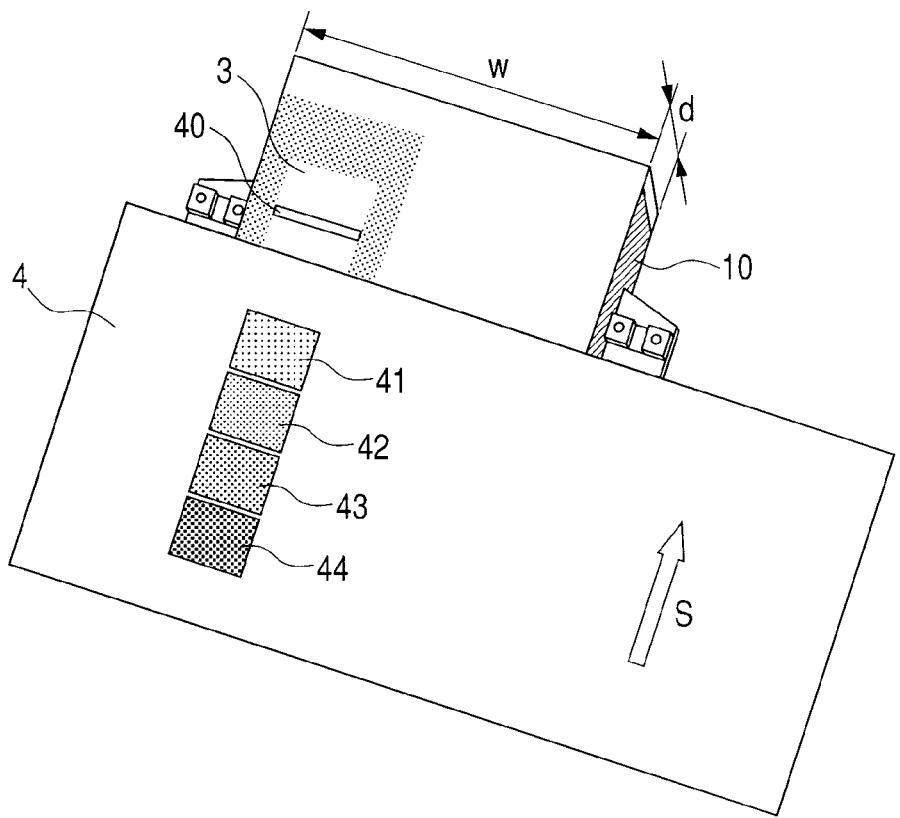
FIG. 1 is a perspective view illustrating a spectral colorimetric apparatus according to Embodiment 1 of the present invention.
Figure 2:
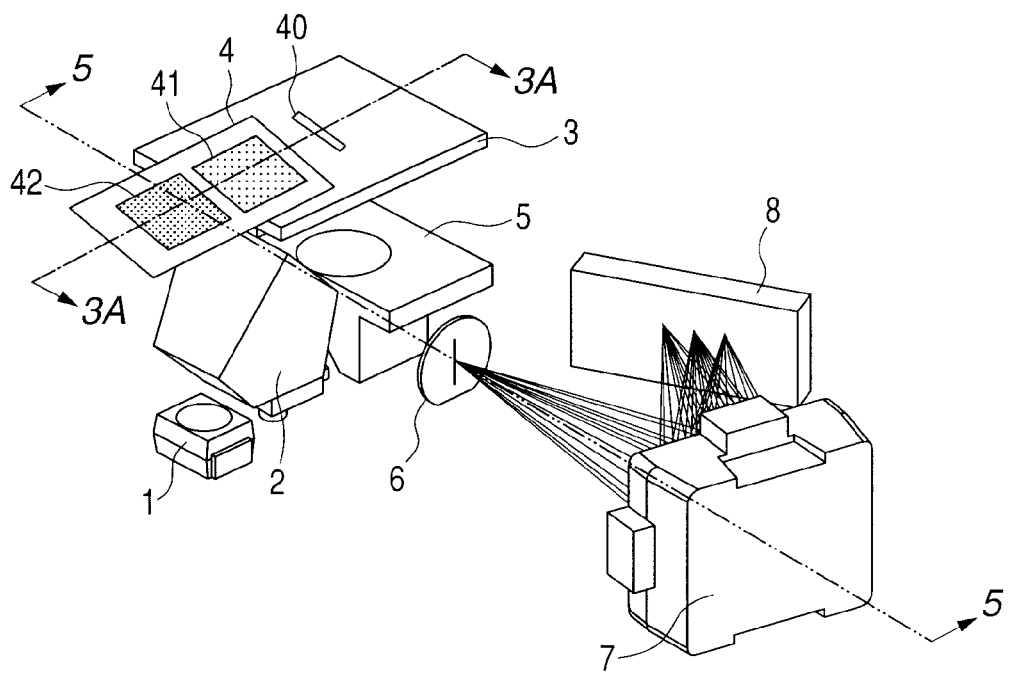
FIG. 2 is an internal perspective view of the spectral colorimetric apparatus according to Embodiment 1 of the present invention.

FIG. 1 is a perspective view illustrating the spectral colorimetric apparatus using a diffraction element, according to Embodiment 1 of the present invention. FIG. 2 is an internal perspective view of the spectral colorimetric apparatus.

In FIG. 2, reflection light (light beam to be tested) diffused by and reflected on a test subject 4 on a detection surface, which is illuminated by an illumination unit including a light source 1 and an illumination optical element 2, is guided to a stop 6 through a guiding optical element 5. The light having passed through the stop 6 is spectrally condensed by a concave surface reflection type diffraction element 7 and imaged for each wavelength on a light receiving surface of a light receiving element array 8 to form a stop image.

The light receiving element array 8 may convert a light quantity for each wavelength into an electrical signal, to thereby obtain spectral intensity information. The spectral intensity information obtained in the spectral colorimetric apparatus is transmitted to an analyzing apparatus (not shown). The analyzing apparatus may serve as a colorimetric apparatus for obtaining absolute chromaticity of the test subject from an internal table based on the input spectral intensity information.

Figure 6A:
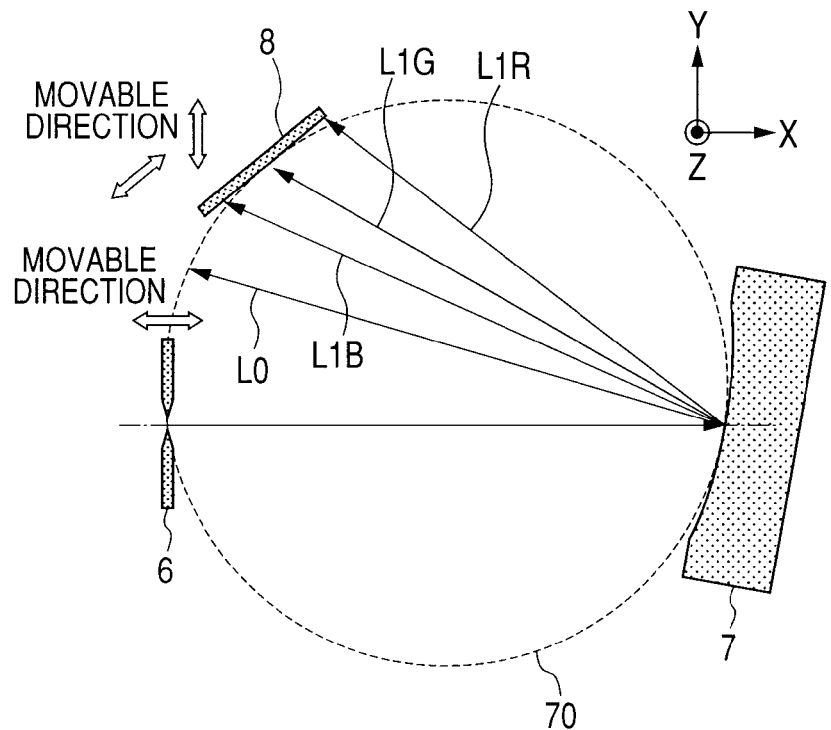
FIG. 6A is a principal cross sectional view illustrating a spectral unit of the spectral colorimetric apparatus according to Embodiment 1 of the present invention.

In this embodiment, a Rowland type spectral device structure, which is a simple structure and effective for a reduction in size, is employed. In the Rowland type spectral device, as illustrated in FIG. 6A, the stop 6 and the concave surface reflection type diffraction element 7 are provided on a Rowland circle 70. Diffraction light for each wavelength is imaged at a predetermined position on the Rowland circle 70. When the light receiving element array 8 is provided at the position, a spectral intensity distribution may be simultaneously detected.

As illustrated in FIGS. 1 and 2, for example, desired color patches (patches for chromaticity adjustment) 41, 42, 43, and 44 are printed on the test subject 4 to be measured. The illumination unit for illuminating the color patches includes the light source 1 and the illumination optical element (optical element having total reflection surface and refractive surface) 2. The color patches 41, 42, 43, and 44 are sequentially moved in a direction indicated by an arrow S illustrated in FIG. 1 to be illuminated.

(Light Source)

In this embodiment, a white light emitting diode (white LED), for example, an ultraviolet LED excitation type white LED, is used as an illumination light source (light source 1).

(Illumination Optical System)

An illumination optical system (illumination optical element) is described with reference to FIGS. 3A and 3B.

An LED generally has a predetermined orientation characteristic based on an element structure thereof. Therefore, an illumination optical element 2 is employed to improve illumination efficiency, to thereby uniformly illuminate the detection surface and reduce a variation in light quantity due to the rising of the test subject.

The light source 1 is an LED which is generally called a top-view type, which emits light in a direction perpendicular to an electrical mounting board (not shown) onto which the light source 1 is attached. The illumination optical element 2 is also attached onto the electrical mounting board to illuminate the detection surface 4. The detection light beam which is reflected and diffused on the detection surface 4 is guided to a spectral optical system through a guiding optical system.

The LED serving as the light source 1 has an orientation angle characteristic in which a light quantity in a direction close to a plane normal to a light emitting surface is maximum and the light quantity gradually reduces as a tilt from the plane normal increases. Therefore, as illustrated in FIG. 3A, Light Lp1 having a maximum intensity is entered into the illumination optical element located immediately above the light source 1 from the vicinity of the center of the light emitting surface of the light source 1. When an incident surface 2a of the illumination optical element 2 is tilted in a detection surface direction, a light beam entered into the incident surface 2a is refracted to become light Lp2. The light having the maximum intensity is bent in the detection surface direction to become light Lp3, is exited from an exit surface 2b, and reaches the detection surface 4. Another light beam Lp4 exited at a tilt from the plane normal to the light emitting surface is entered into the incident surface 2a, and then is totally reflected on a reflective surface 2c to become light Lp5, is exited from the exit surface 2b, and reaches the test subject 4. Another light beam Lp6 exited at a tilt from the plane normal in a direction opposite to the travelling direction of the light beam Lp4 is entered into the incident surface 2a, and then is exited from an exit surface 2d to become light Lp7 to reach the detection surface 4.

When the light beam having the maximum intensity is bent at the incident surface 2a of the illumination optical element 2 as described above, the light beam having the maximum intensity may be guided to the detection surface 4 without tilting the attaching board. Further, the light beams exited at the angles relative to the light beam having the maximum intensity are guided to the detection surface 4 by the total reflective surface action and the refractive surface action, to reduce a change in illumination due to a variation in position in a case where the test subject 4 flutters on the detection surface 4.

Table 1 illustrates a numerical embodiment with respect to the illumination optical system.

Figure 3A:
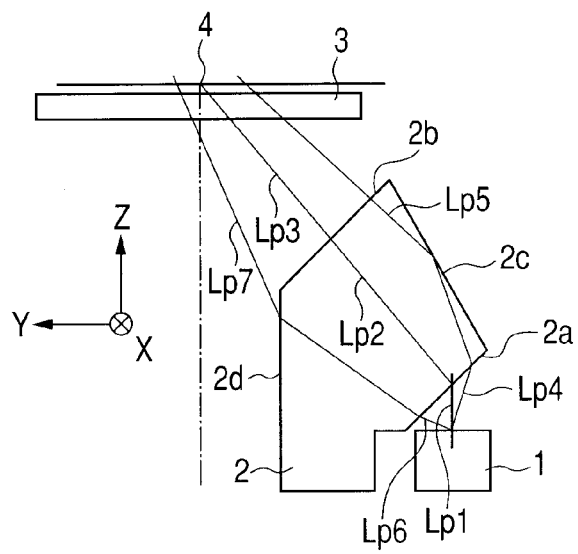
FIG. 3A is a principal cross sectional view (taken along the line 3A-3A of FIG. 2) illustrating an illumination optical system of the spectral colorimetric apparatus according to Embodiment 1 of the present invention.
Figure 3B:
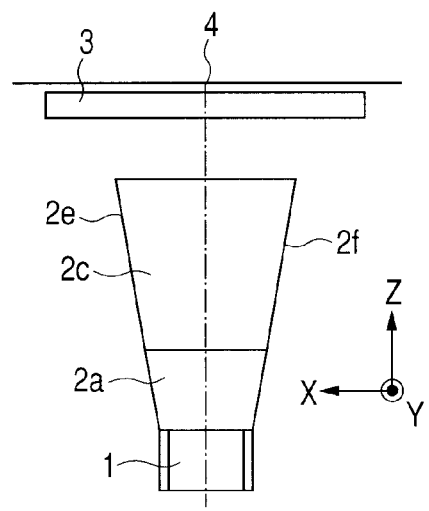
FIG. 3B is a principal view illustrating the illumination optical system of the spectral colorimetric apparatus according to Embodiment 1 of the present invention illustrated in FIG. 3A viewed in Y-axis direction.

In a coordinate system illustrated in FIGS. 3A and 3B, rotating angles about respective X-, Y-, and Z-axes are assumed to be (α, β, γ).

An origin of the coordinate system is set to the center of the detection surface.

TABLE 1

| | Coordinates | Rotating angles (°) |
|---|---|---|
| Detection surface (center) 4 | (0, 0, 0) | (0, 0, 0) |
| Light emitting point center | (0, −8, −11) | (0, 0, 0) |
| Illumination optical element surface 2a | (0, −8, −9.5) | (−45, 0, 0) |
| Illumination optical element surface 2b | (0, −3.5, −5.5) | (−45, 0, 0) |
| Illumination optical element surface 2c | (0, −8, −6.5) | (60, 0, 0) |
| Illumination optical element surface 2d | (0, −2.5, −8) | (90, 0, 0) |
| Illumination optical element surface 2e | (1.46, −8, −11) | (0, −80, 0) |
| Illumination optical element surface 2f | (−1.46, −8, −11) | (0, 80, 0) |

Each of the surfaces of the illumination optical element is flat. The illumination optical element 2 is a plastic optical element made of acrylic and manufactured by injection molding.

Figure 4:
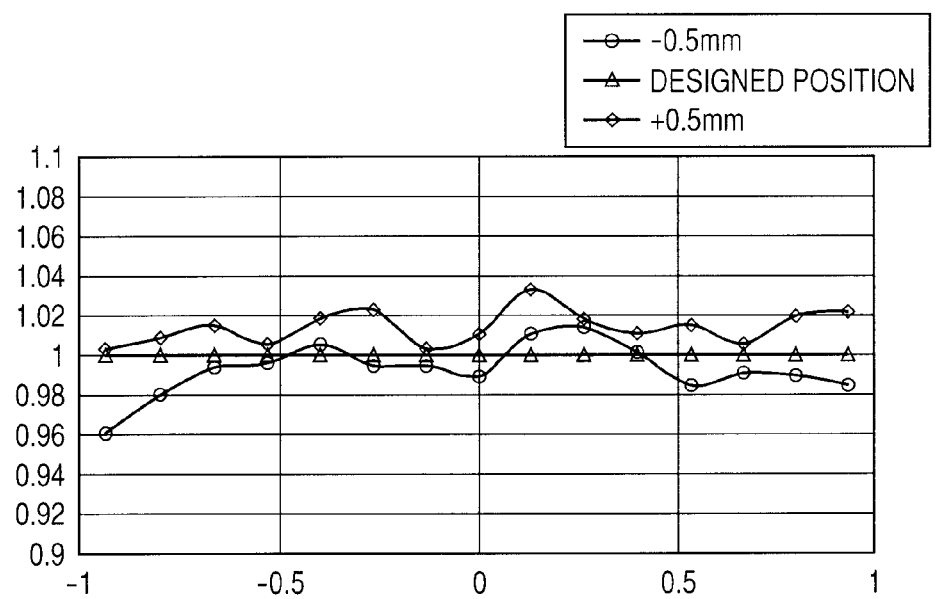
FIG. 4 is a graph illustrating a variation in light quantity of the illumination optical system of the spectral colorimetric apparatus according to Embodiment 1 of the present invention, depending on a variation in test subject position (height direction).

FIG. 4 is a graph illustrating the light quantities at respective positions on the test subject with respect to the center position of the rectangular read region 40 on the detection surface 4 in a direction S of the movement of the test subject 4, with a parameter of deviation in a height direction of the test subject 4 from the detection surface 4 (a direction away from the cover glass 3). The light quantity in a case where the test subject is located on the detection surface 4 is set as 1 for normalization. As is apparent from the graph, even when the test subject is fluctuated relative to the position of the detection surface 4 by ±0.5 mm, excellent correction is achieved because a variation in light quantity is smaller than 3%.

In this embodiment, the illumination optical system described above is employed as a best system. However, the present invention is not limited to the system. Even when any illumination optical system is employed, an effect obtained by the present invention is effective.

As illustrated in FIG. 5, the guiding optical element 5 is a light guide material for guiding reflection light from the test subject 4 to the stop 6. A read region on the detection surface 4 is defined by the stop 6 having a rectangular aperture and is long in a direction perpendicular to the moving direction (arrow S) of the test subject on the detection surface 4 and is narrow in the moving direction thereof. The guiding optical element 5 is a condensing element which exhibits an anamorphic power having a condensing function in a direction (width direction of stop 6) parallel to the spectral direction, to thereby form a substantially linear image by the stop 6.

The detection surface 4 and the stop 6 have substantially a conjugate relationship in a cross section (width direction of the stop 6) parallel to a spectral direction. Therefore, even when the height position of the test subject is varied relative to the detection surface 4, a change in light quantity is small, and hence stable measurement may be achieved. The guiding optical element 5 has a structure to ensure a numerical aperture (NA) equal to or larger than an effective width of a concave surface reflection type diffraction element 7 of a spectral unit in the stop width direction and to condense light at the front and back of the stop 6, to thereby ensure the amount of movement of the stop 6 during focus adjustment.

The light beam to be tested is bent by the guiding optical element in a direction perpendicular to the detection surface 4 to make the detection surface and a spectral plane of the spectral unit parallel to each other, to thereby reduce the thickness of the spectral colorimetric apparatus.

Within the spectral plane, a principal ray of the light beam enters the spectral optical system obliquely with respect to a straight line joining the center of the light receiving element array 8 with the surface vertex of the spectral element to make a light receiving surface of the light receiving element array 8 and the spectral plane orthogonal to each other, to thereby reduce the thickness of the spectral colorimetric apparatus.

Note that the spectral plane is defined as a plane including a principal ray of an incident light beam on a spectral element (which is a concave surface reflection type diffraction element in this embodiment, and may be a transmission type diffraction element or a spectral prism) and respective principal rays of light beams obtained by diffracting (diffusing) the principal ray of the incident light beam by the spectral element.

In this embodiment, a composite element having a function of bending the optical path by total reflection and a function of condensing by a refractive surface is assumed as the guiding optical element. However, the functions may be separated from each other to provide a guiding optical element including an optical path folding mirror and a condensing lens.

Table 2 illustrates a specific numerical embodiment with respect to the guiding optical element.

In a coordinate system illustrated in FIG. 5, rotating angles about respective axes are expressed by ($\alpha$, $\beta$, $\gamma$).

The center of the detection surface is set as an origin of the coordinate system.

TABLE 2

| | | | Curvature radius (mm) | |
|---|---|---|---|---|
| | Coordinates | Rotating angles (°) | X-Y cross section | X-Z cross section |
| Detection surface (center) 4 | (0, 0, 0) | (0, 0, 0) | ∞ (Flat) | |
| Guiding optical element surface 5a | (0, 0, −6.0) | (0, 0, 0) | 3.85 (Spherical) | |
| Guiding optical element surface 5b | (0, 0, −9.0) | (0, 45, 0) | 10.3 | ∞ |
| Guiding optical element surface 5c | (2.1, 0, −9.0) | (0, 90, 0) | ∞ (Flat) | |
| Stop 6 | (10, 0, −9.0) | (0, 90, 0) | ∞ (Flat) | |

(Spectral Optical System)

As illustrated in FIG. 6A, light passing through the stop 6 is spectrally condensed by the concave surface reflection type diffraction element 7 and imaged for each wavelength on the light receiving element array 8 to form a stop image. FIG. 6A illustrates first-order diffraction light L1B, L1G, and L1R and zero-order diffraction light L0.

A Si photo diode array is generally used as the light receiving element array 8. Multiple light receiving pixels are laterally arranged on the light receiving surface of the light receiving element array 8. Each of the light receiving pixels may output, as a detection signal, an intensity of the stop image obtained by condensing for each wavelength. The detection signal is detected as a signal corresponding to each wavelength by a signal processing circuit (not shown), and hence corresponding chromaticity may be calculated. In view of the structure of the Si photo diode array, the spectral sensitivity is higher close to a near-infrared region and the spectral sensitivity reduces as the wavelength shortens. The signal processing circuit has a configuration capable of generating a processing signal in consideration of the spectral sensitivity of the light receiving element array 8.

Figure 6B:
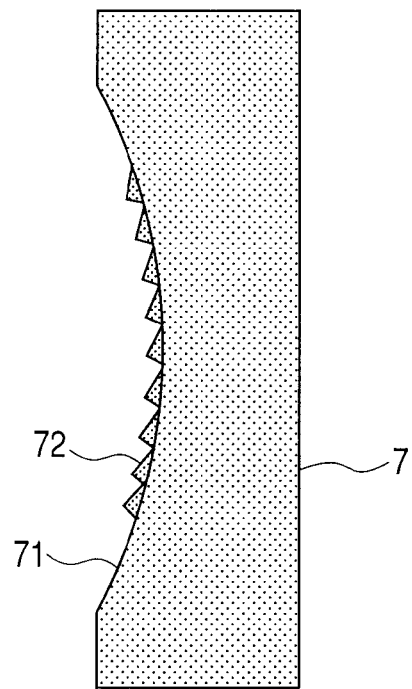
FIG. 6B is a schematic view illustrating a concave surface reflection type diffraction element of the spectral colorimetric apparatus according to Embodiment 1 of the present invention.

As illustrated in FIG. 6B, the concave surface reflection type diffraction element 7 includes blaze diffraction gratings provided on an anamorphic surface having different curvatures in the Y-direction and the Z-direction.

In the Rowland type spectral device structure, the concave surface reflection type diffraction element 7 generally includes a spherical surface which serves as a base surface. Therefore, there has been a problem that, imaging states in the spectral direction and a direction orthogonal to the spectral direction are significantly different from each other, and hence large astigmatism occurs to degrade imaging performance, to thereby deteriorate the resolution of the spectral device. This problem occurs in principle and thus may not be completely eliminated in view of the feature. However, when the curvatures of the concave surface reflection type diffraction element 7 in the spectral direction and the direction orthogonal to the spectral direction are set different from each other (that is, the surface of the concave surface reflection type diffraction element 7 is set an anamorphic surface), an image plane tilt in the direction orthogonal to the spectral direction may be changed between a short wavelength and a long wavelength. Therefore, necessary and sufficient imaging performance may be obtained. Thus, the base surface of the concave surface reflection type diffraction element is configured as an anamorphic surface.

The concave surface reflection type diffraction element 7 is manufactured as follows. A plastic optical element is formed by injection molding and a reflective film made of Al and a high-reflection film made of $SiO_2$ are formed on the plastic optical element by vapor deposition. The concave surface reflection type diffraction element 7 may be manufactured by direct ion beam processing or conventional lithography processing on an optical substrate such as a quartz substrate.

The concave surface reflection type diffraction element 7 is described in detail.

FIG. 6B is a cross sectional diagram illustrating the concave surface reflection type diffraction element 7 in the spectral direction. A large number of fine blaze diffraction gratings 72 are provided on an arc-shaped base surface 71. (Note that the blaze diffraction gratings 72 are exaggerated for the purpose of explanation).

Tables 3 and 4 illustrate specifications of the spectral device and the shape of the concave surface reflection type diffraction element 7 in this embodiment.

Further, Table 5 illustrates the arrangement of the spectral unit. In a coordinate system which corresponds to the coordinate system illustrated in FIG. 6A, rotating angles about respective axes are expressed by ($\alpha$, $\beta$, $\gamma$).

An origin of the coordinate system is the center of the stop.

TABLE 3

| (Spectral Device Specifications) | |
|---|---|
| Spectral range | 380 nm to 780 nm |
| Light source | Ultraviolet LD excitation white LED |
| Stop width | 60 μm |
| Detection element | Si photo diode array |
| Diffraction order m | 1 |
| Pixel pitch of element | 25 μm |
| Wavelength resolution | 3.3 nm |

TABLE 4

| (Diffraction Element Specifications) | |
|---|---|
| Base meridional line curvature radius [mm] | 17.5 |
| Base sagittal line curvature radius [mm] | 15.45 |
| Grating pitch P [μm] | 2.52 |
| Grating height h [μm] | 0.25 |

TABLE 4-continued (Diffraction Element Specifications)

| | |
|---|---|
| Incident angle α [°] | 12 |
| Reflective film | Al-based multilayer film |
| Effective diameter [mm] | 7 |

TABLE 5

(Arrangement of Spectral Unit)

| | Coordinates | Rotating angles (°) |
|---|---|---|
| Stop 6 | (4.331, 9.881, 0) | (0, 0, 0) |
| Concave Surface Reflection Type Diffraction Element 7 | (17.118, 0, 0) | (−12, 0, 0) |
| Light Receiving Element Array (center) 8 | (0, 0, 0) | (−62.6, 0, 0) |

(Cover glass (0.3 mm) and a resin layer (0.45 mm), which are not shown, are provided on a surface of the light receiving element array 8.)

The Rowland type spectral device is used, and hence a Rowland circle radius is 8.75 mm and a curvature radius of a meridional line of the anamorphic base surface of the concave surface reflection type diffraction element 7 within a plane including the Rowland circle is double the Rowland circle diameter, that is, 17.5 mm. A curvature radius of a sagittal line orthogonal to the meridional line 15.45 mm. An effective diameter is 7 mm and NA is 0.4.

The concave surface reflection type diffraction element 7 is manufactured by plastic injection molding using a mold formed by cutting. Alternatively, the concave surface reflection type diffraction element 7 may be manufactured by directly cutting a base material. Alternatively, the concave surface reflection type diffraction element 7 may be manufactured by a replica method of pressing molten glass to a mold formed by cutting. In any of the cases, a multilayer film including a metal film made of Al as a base film is finally formed on the grating surface by vapor deposition.

In FIG. 6A, there may be a case where an image of the stop 6 blurs on the light receiving element array 8 because of disposition precision among the stop 6, the concave surface reflection type diffraction element 7, and the light receiving element array 8 and surface precision of the concave surface reflection type diffraction element 7. In view of this, the stop 6 may be held by a holder so as to be shiftable in a light beam traveling direction. From the same reason, there may be a case where a reaching position of the image of the stop on the light receiving element array 8 is deviated. Therefore, the light receiving element array 8 may be two-dimensionally adjustable (in Y- and Z-directions) on a reference attachment surface perpendicular to the spectral plane, to be adjusted in position.

According to the present invention, the spectral plane of the spectral optical system is defined by a plane including a principal ray of an incident light beam on an arbitrary spectral element (which is a concave surface reflection type diffraction element, and may be a transmission type diffraction element or a spectral prism in this embodiment) and respective principal rays of light beams which are obtained by diffracting (diffusing) the principal ray of the incident light beam by the spectral element.

When the spectral plane and the detection surface are provided so as to be parallel to each other, the thickness of the spectral colorimetric apparatus in the direction perpendicular to the detection surface may be effectively reduced.

When the principal ray of the light beam enters the spectral optical system within the spectral plane obliquely with respect to the straight line joining the center of the light receiving element array 8 with the surface vertex of the spectral element to make the light receiving surface of the light receiving element array 8 and the spectral plane orthogonal to each other, the thickness of the spectral colorimetric apparatus may be effectively reduced.

Specifically, the guiding optical system 5 is provided with a function for folding an optical path of the reflection light beam from the detection surface 4 in the direction perpendicular to the normal to the detection surface 4, to thereby realize the structure in which the detection surface 4 and the spectral plane are parallel to each other.

The spectral plane may have an angle in a non-dispersion direction depending on an incident angle on the spectral element. In this embodiment, the spectral plane of the spectral unit and the detection surface are parallel to each other. However, a margin of error of approximately ±10° may be allowed without departing from requirements in this embodiment.

When the thickness of the spectral colorimetric apparatus in the direction of the plane normal to the detection surface 4 is denoted by d and a maximum width of the spectral colorimetric apparatus in the direction parallel to the detection surface 4 is denoted by W, it is desirable to configure the spectral colorimetric apparatus so as to satisfy the following expression.

$$0.1 < d/W < 1 \tag{1}$$

When d/W exceeds an upper limit value of the conditional expression (1), a reduction in thickness may not be practically achieved. When d/W exceeds a lower limit value of the conditional expression (1), an area necessary for mounting the spectral colorimetric apparatus becomes too large when incorporated in another device, making the spectral colorimetric apparatus difficult to use. When d/W is within a range satisfying the conditional expression (1), the spectral colorimetric apparatus may be effectively reduced in thickness and size.

In this embodiment, the thickness d of the spectral colorimetric apparatus in the direction of the plane normal to the detection surface 4 is 15 (mm) and the maximum width W of the spectral colorimetric apparatus within the plane parallel to the detection surface 4 is 40 (mm), and hence d/W=0.375. Therefore, d/W satisfies the conditional expression (1), and hence a sufficient reduction in thickness may be achieved.

In this embodiment, the illumination optical element which employs the white LED as the light source 1 is used to reduce the size of the illumination optical system. The single optical element including the total reflection surface and the refractive surface is used as the guiding optical system, to thereby achieve the reduction in size.

In this embodiment, as illustrated in FIG. 2, the longitudinal direction of a rectangular read region 40 on the detection surface 4 which is defined by the stop 6 is perpendicular to a conveying direction of the test subject defined within the detection surface 4. Therefore, when a color patch 41, 42, 43, 44 is assumed as the test subject, a width of the color patch in the conveying direction may be reduced. Thus, a larger number of color patches may be formed on a single paper sheet to achieve higher-precision color calibration.

In this embodiment, as illustrated in FIG. 2, the light source 1 and the light receiving element array 8 are provided in opposite and distant positions across a reference line 5-5 joining the center of the stop 6 with the surface vertex of the concave surface reflection type diffraction element 7, and hence direct flare light from the light source may be reduced while the apparatus is reduced in size. The flare light becomes noise to cause a chromaticity difference during chromaticity measurement, and hence it is desirable to minimize the flare light.

In this embodiment, the Rowland type spectral device is used for the spectral unit. Even when a transmission type diffraction element structure or a general multi-wavelength spectral device structure is employed for the spectral unit, the spectral unit may be embodied without impairing availability.

The reason why the Rowland type multi-wavelength spectral device is used in this embodiment is that, the Rowland type multi-wavelength spectral device is easily reduced in size by reducing the Rowland circle and may be made significantly smaller in size than other multi-wavelength spectral devices.

(Method of Adjusting Spectral Colorimetric Apparatus)

A method of adjusting the spectral colorimetric apparatus is described with reference to FIG. 6A.

When the spectral colorimetric apparatus is assembled, it is easy to assume that mere mechanical alignment does not attain excellent performance, due to a positioning error of the stop 6 and an attachment error of the concave surface reflection type diffraction element 7 or the light receiving element array 8. Therefore, in this embodiment, optical adjustment is performed on two elements, that is, four axes in total in the diffraction unit.

Hereinafter, a specific element adjusting method is described step by step.

(First Process)

The stop 6 and the light receiving element array 8 are temporarily incorporated in a casing and the concave surface reflection type diffraction element 7 is fixed based on a mechanical reference. The position of the light receiving element array 8 in the direction of the plane normal to the light receiving surface is regulated and may be movable only within the plane perpendicular to the plane normal. Light beams having specific wavelengths from an external light source 1 are made incident through the guiding optical element 5. In this embodiment, a light beam having a wavelength of 450 nm and a light beam having a wavelength of 650 nm from a spectral light source (having wavelength resolution of 5 mm) are guided. For each of the wavelengths, the output of the light receiving element array 8 is observed while the stop 6 is moved in forward and backward directions along the reference line 5-5 joining the center of the stop 6 with the surface vertex of the concave surface reflection type diffraction element 7. The position of the stop 6 that maximizes the output in each of the wavelengths is determined and held. Therefore, the imaging state on the light receiving element array 8 may be adjusted. When the wavelengths are set close to a minimum wavelength and a maximum wavelength in a spectral range of the spectral colorimetric apparatus, variations in the imaging state is compensated over the entire region.

In order to perform this process, as described above with reference to the embodiment, it is important to make a design to reduce variations in light quantity which is caused by vignetting by the stop 6 in the case where the stop 6 is moved in the forward and backward directions by the function of the guiding optical system 5. The reason is that, when such a requirement is not satisfied, a variation in light quantity due to a deviation of focusing and a variation in light quantity due to the movement of the stop 6 may not be distinguished from each other.

(Second Process)

After the completion of the first process, the stop 6 is rotated about the reference line 5-5 to detect the position of the stop 6 at which a peak of the output waveform of the light receiving element array 8 is sharper. Therefore, an incidence of a light beam having another wavelength to a pixel due to the rotation of the stop 6 or the rotation of the light receiving element array 8 may be reduced. This process may be executed with only any one of the wavelengths used in the first process.

(Third Process)

After the completion of the second process, the pixel position adjustment on the light receiving element array 8 is performed with the light beams of the two wavelengths used in the first process. A light beam having the first wavelength is guided and the light receiving element array 8 is shifted in the spectral direction such that an output of a specified pixel "A" on the light receiving element array is maximum. With such a state, a light beam having the second wavelength is guided and a pixel "B" having a maximum output is determined. A simple Rowland type polychromator generally has distortion in view of design, and a pitch of the light beams of the respective wavelengths does not become regular on the light receiving element array 8. Therefore, a deviation of a distance between the pixel "A" and the pixel "B" from a design value is electrically corrected.

(Fourth Process)

After the completion of the third process, a light beam having the center wavelength (550 nm in this embodiment) of the spectrum of the spectral colorimetric apparatus is made incident from the external light source. The light receiving element array 8 is shifted in the direction orthogonal to the spectral direction to detect, as a best position, a position in which the light quantity of a pixel corresponding to 550 nm is maximum. Then, the light receiving element array 8 is finally fixed.

A best spectral performance may be obtained through the four adjustment processes described above. The adjusting method is described step by step. However, the four processes are not necessarily performed in the stated order. The processes may be exchanged or a part of the processes may be omitted.

Embodiment 2

Example of Spectral Colorimetric Apparatus Using Planer Transmission Type Diffraction Element This embodiment illustrates an example of a spectral colorimetric apparatus using a planer transmission type diffraction element for a spectral optical system.

Figure 7:
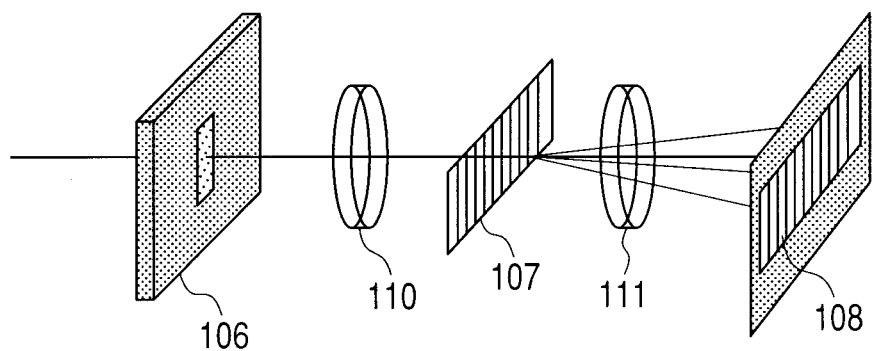
FIG. 7 is a principal cross sectional view illustrating a spectral colorimetric apparatus according to Embodiment 2 of the present invention.

FIG. 7 is a perspective view illustrating a spectral optical system using a planer transmission type diffraction element in a spectral colorimetric apparatus according to Embodiment 2 of the present invention.

Embodiment 2 is different from Embodiment 1 in that the spectral element included in the spectral optical system is a planer transmission type diffraction element 107. The illumination optical system and the guiding optical system are the same as in Embodiment 1.

In this embodiment, a spectral device structure which is a simple structure and effective for a reduction in size is employed. A detection optical system including a stop 106, a condenser lens element 110 for detection, a planer transmission type diffraction element 107, and an imaging lens 111 is configured such that a light beam having a predetermined wavelength is imaged at a predetermined position. When a light receiving element array 108 is provided in the predetermined position, a spectral intensity distribution may be obtained at the same time.

The test subject 4 is illuminated by the same illumination optical system as in Embodiment 1. Reflection light from the illuminated test subject 4 is guided to the stop 106 through the guiding optical system. Light having passed through the stop 106 is converted into parallel light beams by the condenser lens element 110 for detection. Then, the guided light beam is spectrally separated by the planer transmission type diffraction element 107. The guided light beam is condensed by the imaging lens 111 to form a stop image on the light receiving element array 108 for each wavelength.

The light receiving element array 108 converts the light quantity at each wavelength into an electrical signal and transmits the electrical signal to an analyzing apparatus (not shown). The analyzing apparatus obtains chromaticity of the test subject 4 based on an internal table and the input spectral intensity information.

The planer transmission type diffraction element 107 includes a large number of fine blaze gratings provided on a flat base surface.

Tables 6 and 7 below show specifications of the spectral colorimetric apparatus and the shape of the planer transmission type diffraction element 107 according to this embodiment.

TABLE 6

(Spectral Colorimetric Apparatus Specifications)

| | |
|---|---|
| Spectral range | 350 nm to 750 nm |
| Light source | Ultraviolet LD excitation white LED |
| Stop width | 60 μm |
| Detection element | Si photo diode array |
| Diffraction order m | 1 |
| Pixel pitch of element | 25 μm |
| Wavelength resolution | 3.3 nm |
| Focal length of condenser lens element for detection | 37.1 mm |
| Focal length of imaging lens | 37.1 mm |

TABLE 7

(Diffraction Element Specifications)

| | |
|---|---|
| Base meridional line curvature radius (mm) | ∞ |
| Base sagittal line curvature radius (mm) | ∞ |
| Refractive index of base material | 1.539 |
| Grating pitch P (μm) | 5.04 |
| Grating height h (μm) | 0.650 |
| Blaze angle θb (°) | 7.3 |
| Incident angle α (°) | 0 |

Even in this embodiment, when the same guiding optical system as in Embodiment 1 is used, the detection surface and the spectral plane may be made parallel to each other, and hence the thickness in the direction perpendicular to the detection surface may be effectively reduced.

In the system according to this embodiment, the thickness d in the direction perpendicular to the detection surface is 15 (mm) and the maximum width W within the plane parallel to the detection surface is 80 (mm), and hence d/W=0.188. Therefore, d/W satisfies the conditional expression (1).

As described above, even in the case of the spectral colorimetric apparatus using the transmission type diffraction element, the thickness of the spectral colorimetric apparatus in the direction perpendicular to the detection surface may be effectively reduced.

As described above, even when the general multi-wavelength spectral device structure is employed for the spectral colorimetric apparatus, the spectral colorimetric apparatus may be embodied without impairing availability.

Embodiment 3

Figure 8:
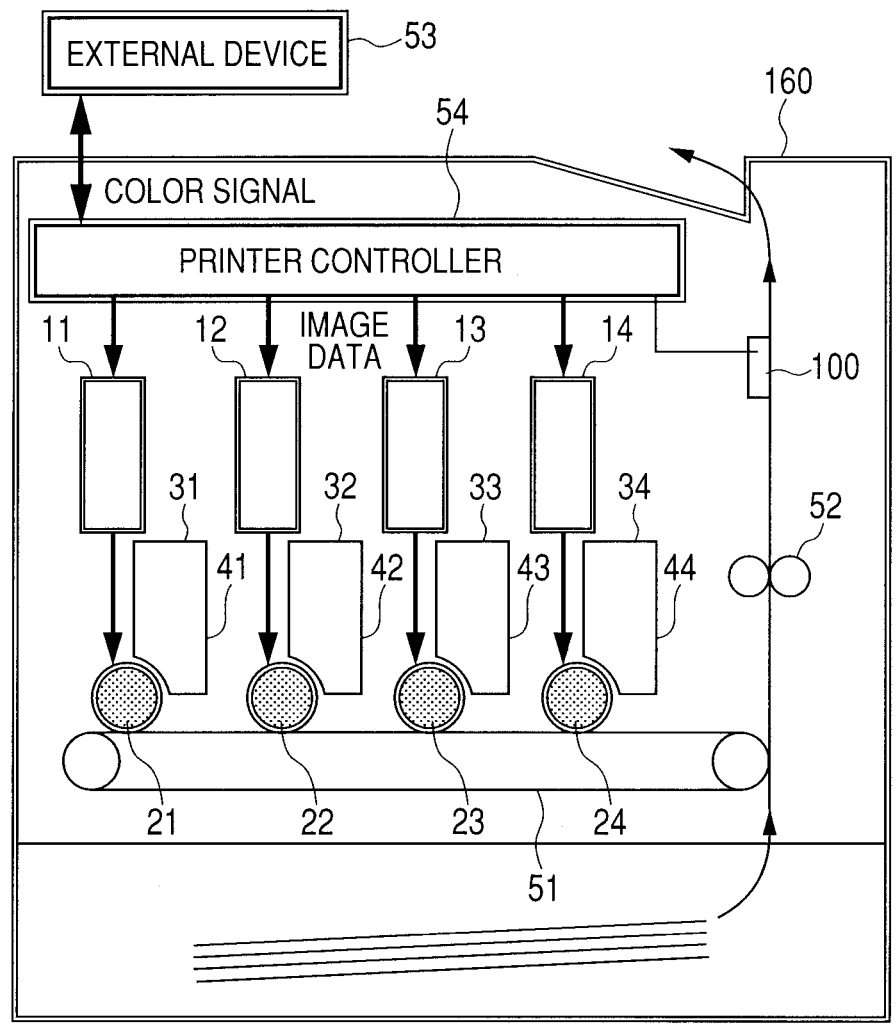
FIG. 8 is a principal cross sectional diagram illustrating a color image forming apparatus according to an embodiment of the present invention.
Figure 9:
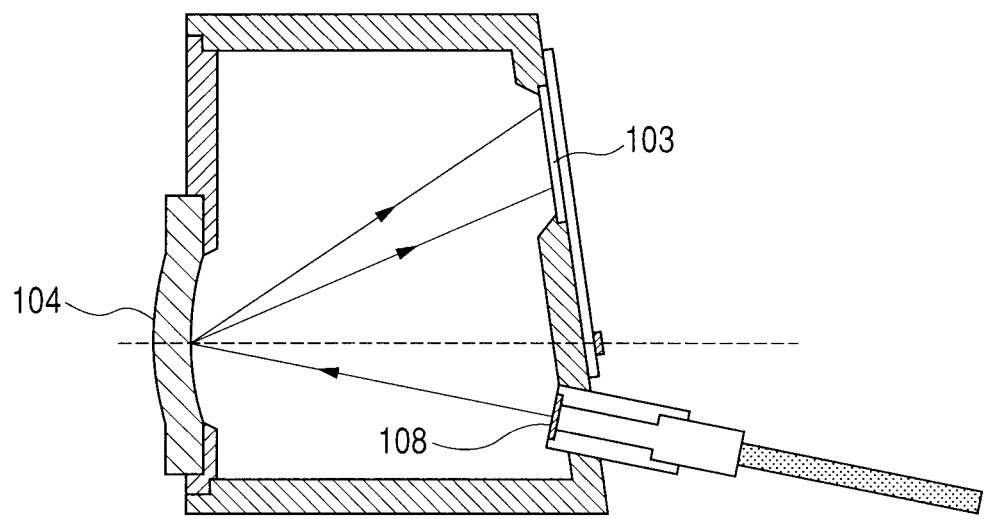
FIG. 9 is a principal cross sectional view illustrating a conventional spectral colorimetric apparatus.

FIG. 8 is a principal schematic diagram illustrating a color image forming apparatus according to an embodiment of the present invention. This embodiment illustrates a tandem type color image forming apparatus, in which four optical scanning apparatuses are arranged to record image information in parallel on surfaces of photosensitive drums each serving as an image bearing member. The color image forming apparatus 160 includes optical scanning apparatuses 11, 12, 13, and 14, photosensitive drums 21, 22, 23, and 24 each serving as the image bearing member, developing devices 31, 32, 33, and 34, an intermediate transferring belt 51, and a fixing device 52.

In FIG. 8, respective color signals of R (red), G (green), and B (blue) are input from an external device 53, such as a personal computer, to the color image forming apparatus 160. The color signals are converted into respective image data (dot data) of C (cyan), M (magenta), Y (yellow), and B (black) by a printer controller 54 in the color image forming apparatus 160. The image data are separately input to the optical scanning apparatuses 11, 12, 13, and 14. Light beams 41, 42, 43, and 44 which are modulated according to the respective image data are emitted from the optical scanning apparatuses. The photosensitive surfaces of the photosensitive drums 21, 22, 23, and 24 are scanned with the light beams in the main scanning direction.

In the color image forming apparatus 160 according to this embodiment, the four optical scanning apparatuses 11, 12, 13, and 14 are arranged corresponding to the respective colors of C (cyan), M (magenta), Y (yellow), and B (black). The image signals (image information) are recorded in parallel on the surfaces of the photosensitive drums 21, 22, 23, and 24, to thereby print a color image at high speed.

According to the color image forming apparatus 160 according to this embodiment, as described above, latent images of the respective colors are formed on the corresponding surfaces of the photosensitive drums 21, 22, 23, and 24 using the light beams based on the respective image data from the four scanning optical apparatuses 11, 12, 13, and 14. After that, the latent images are developed by the respective developing devices and the respective colors are multiply transferred onto the intermediate transport belt 51. Then, the image is transferred to a recording material and formed on the recording material by the fixing device 52.

In the color image forming apparatus 160, a colorimetric apparatus 100 for chromaticity detection is provided immediately after the fixing device 52 on a conveying path of the recording material and facing to the image forming surface of the recording material. The colorimetric apparatus has the structure described in Embodiment 1. The colorimetric apparatus 100 detects chromaticity of a color patch which is formed on and fixed onto the recording material by the image forming apparatus 160. The chromaticity of the color patch fixed onto the recording material is measured because color matching is then performed in view of a change in chromaticity due to fixing. The result obtained by the detection is transferred to the printer controller 54. The printer controller 54 determines whether or not the output color reproduction of the single-color patch is appropriate. When a chromaticity difference between the output color reproduction of the single-color patch and chromaticity instructed by the printer controller is within a predetermined range, the color calibration is completed. When the chromaticity difference is outside the predetermined range, the printer controller performs the color calibration based on the chromaticity information until the chromaticity difference falls within the predetermined range.

As describe above, when the color sensor according to the present invention is introduced to an image forming apparatus, a higher degree of calibration may be performed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2009-110884, filed on Apr. 30, 2009, and 2010-077821, filed on Mar. 30, 2010, which are hereby incorporated by reference herein in their entirety.

What is claimed is:

1. A spectral colorimetric apparatus for detecting a color of an image of a test subject, the spectral colorimetric apparatus comprising:
    an illumination optical system that illuminates the test subject located on a detection surface;
    a spectral optical system including a spectral element that spectrally separates a light beam diffused by the test subject and a light receiving element array that detects a spectral intensity distribution of the light beam spectrally separated by the spectral element; and
    a guiding optical system that guides a light beam diffused by the test subject to the spectral optical system,
    wherein a plane, including a principal ray of a light beam incident on the spectral optical system and a principal ray of a light beam having been spectrally separated by the spectral element, is defined as a spectral plane,
    wherein the detection surface and the spectral plane are parallel to each other, and
    wherein a light receiving surface of the light receiving element array and the spectral plane are orthogonal to each other.

2. A spectral colorimetric apparatus according to claim 1, wherein the spectral optical system further comprises a stop for regulating the light beam diffused by the test subject.

3. A spectral colorimetric apparatus according to claim 2, wherein:
    the guiding optical system bends the light beam diffused by the test subject in a direction perpendicular to an incident direction to the guiding optical system, and
    the detection surface and the stop are conjugate with each other in at least one cross section.

4. A spectral colorimetric apparatus according to claim 2, wherein:
    a conveying direction of the test subject is within a plane including the detection surface, and
    a longitudinal direction of a rectangular read region on the detection surface, which is defined by the stop, is perpendicular to the conveying direction of the test subject.

5. A spectral colorimetric apparatus according to claim 2, wherein:
    a line joining the stop and a surface vertex of the spectral element is set as a reference line, and
    the illumination optical system and the light receiving element array are disposed with the reference line sandwiched therebetween.

6. A spectral colorimetric apparatus according to claim 2, wherein:
    the spectral element comprises a concave surface reflection type diffraction element, and
    the stop, the concave surface reflection type diffraction element, and the light receiving element array provided on a Rowland circle.

7. A spectral colorimetric apparatus according to claim 1, wherein the following condition is satisfied:

$$0.1 < d/W < 1,$$

where d (mm) represents a thickness of the spectral colorimetric apparatus in a direction of a plane normal to the detection surface and W (mm) indicates a maximum width of the spectral colorimetric apparatus within a plane parallel to the detection surface.

8. A color image forming apparatus comprising:
a spectral colorimetric apparatus for detecting a color of an image of a test subject,
wherein the spectral colorimetric apparatus comprises:
an illumination optical system that illuminates the test subject located on a detection surface;
a spectral optical system including a spectral element that spectrally separates a light beam diffused by the test subject and a light receiving element array that detects a spectral intensity distribution of the light beam spectrally separated by the spectral element; and
a guiding optical system that guides a light beam diffused by the test subject to the spectral optical system,
wherein a plane, including a principal ray of a light beam incident on the spectral optical system and a principal ray of a light beam having been spectrally separated by the spectral element, is defined as a spectral plane,
wherein the detection surface and the spectral plane are parallel to each other, and
wherein a light receiving surface of the light receiving element array and the spectral plane are orthogonal to each other.

* * * * *